United States Patent
Tanigawa

(10) Patent No.: US 7,959,571 B2
(45) Date of Patent: Jun. 14, 2011

(54) ULTRASONIC DIAGNOSTIC APPARATUS AND ULTRASONIC DIAGNOSTIC IMAGE GENERATING METHOD

(75) Inventor: Shunichiro Tanigawa, Tokyo (JP)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 1028 days.

(21) Appl. No.: 11/765,707

(22) Filed: Jun. 20, 2007

(65) Prior Publication Data

US 2007/0299344 A1    Dec. 27, 2007

(30) Foreign Application Priority Data

Jun. 23, 2006    (JP) .................................. 2006-174470

(51) Int. Cl.
*A61B 8/00* (2006.01)
(52) U.S. Cl. ...................................... 600/437
(58) Field of Classification Search ................ 600/458
See application file for complete search history.

(56) References Cited

U.S. PATENT DOCUMENTS

| 5,628,322 | A | 5/1997 | Mine |
| 5,724,976 | A | 3/1998 | Mine et al. |
| 5,740,128 | A | 4/1998 | Hossack et al. |
| 6,027,448 | A | 2/2000 | Hossack et al. |
| 2005/0215897 | A1* | 9/2005 | Sakaguchi et al. ............ 600/437 |
| 2007/0149877 | A1* | 6/2007 | Oshiki et al. .................. 600/427 |

FOREIGN PATENT DOCUMENTS

| JP | 2004-057379 | 2/2004 |
| JP | 2005-058587 | 3/2005 |
| JP | 2005-087266 | 4/2005 |
| JP | 2005-118142 | 5/2005 |
| JP | 2005-253852 | 9/2005 |
| JP | 2006116070 | 5/2006 |

* cited by examiner

*Primary Examiner* — Tse Chen
*Assistant Examiner* — Hien Nguyen
(74) *Attorney, Agent, or Firm* — Armstrong Teasdale LLP

(57) ABSTRACT

The invention provides an ultrasonic diagnostic apparatus and an ultrasonic diagnostic image generating method realizing improvement in picture quality to thereby improve diagnosis efficiency in a diagnosis using images. An extracting process of extracting a sound ray vector image extending in a sound ray direction in which an ultrasonic beam is transmitted in an ultrasonic diagnosis image from the ultrasonic diagnosis image is performed. After that, a correcting process is performed so as to eliminate the sound ray vector image extracted by the extracting process from the ultrasonic diagnosis image.

12 Claims, 3 Drawing Sheets

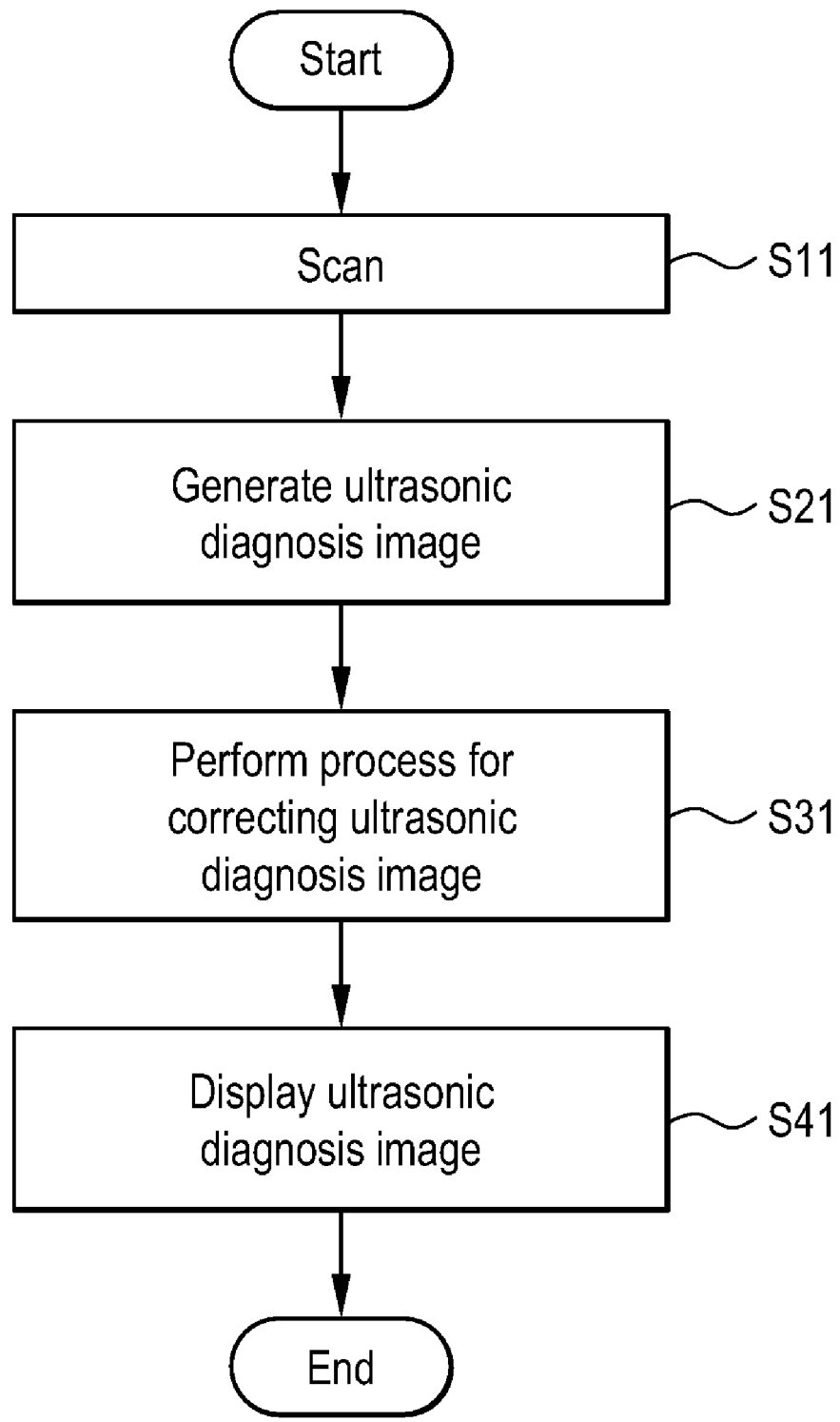

ULTRASONIC DIAGNOSTIC APPARATUS AND ULTRASONIC DIAGNOSTIC IMAGE GENERATING METHOD

CROSS REFERENCE TO RELATED APPLICATIONS

This application claims the benefit of Japanese Application No. 2006-174470 filed Jun. 23, 2006.

BACKGROUND OF THE INVENTION

The present invention relates to an ultrasonic diagnostic apparatus and an ultrasonic diagnostic image generating method and, more particularly, to an ultrasonic diagnostic apparatus and an ultrasonic diagnostic image generating method for performing a scan of transmitting an ultrasonic beam to an image capture region in a subject and receiving an ultrasonic echo reflected from the image capture region and, on the basis of sound ray data obtained by executing the scan, generating an ultrasonic diagnostic image of the image capture region.

An ultrasonic diagnostic apparatus can easily display ultrasonic diagnosis images in a real-time manner at the time of performing a scan, so that it is often used in the medical field for fetal medical check, heart check, and the like.

In the case of displaying an ultrasonic diagnostic image by using the ultrasonic diagnostic apparatus, first, by performing a scan for transmitting an ultrasonic beam to an image capture region in a subject and receiving an ultrasonic echo reflected from the image capture region, sound ray data is obtained. For example, the scan is performed by a sector scan method, a linear scan method, a convex scan method, a radial scan method, or the like.

On the basis of the sound ray data obtained by execution of the scan, an ultrasonic diagnostic image of the image capture region is generated and displayed on a display screen (refer to Patent Documents 1 and 2). The ultrasonic diagnostic apparatus has various display modes such as A mode, B mode, C mode, CFM (Color Flow Mapping) mode, and the like. An ultrasonic diagnosis image corresponding to a mode is displayed. For example, by interpolating sound ray data obtained by the sector scan or convex scan, an ultrasonic diagnosis image is generated and displayed on a display screen (refer to, for example, Patent Document 3).

[Patent Document 1] Japanese Patent Laid-open No. 2005-87266[Patent Document 2] Japanese Patent Laid-open No. 2005-253852[Patent Document 3] Japanese Patent Laid-open No. 2005-58587

However, in an ultrasonic diagnostic image, there is a case that a sound ray vector image is generated as artifact so as to extend in the sound ray direction in which an ultrasonic beam is transmitted. The sound ray vector image is generated because adjacent ultrasonic beams interfere each other when a scan is performed.

In particular, when a color image like a CFM image is generated and displayed as an ultrasonic diagnostic image on a display screen, there is a case such that the inconvenience of generation of a sound ray vector image is conspicuous.

When a sound ray vector image is generated in an ultrasonic diagnostic image as described above, the picture quality deteriorates. Consequently, at the time of conducting a diagnosis with an image, the diagnosis efficiency is low.

SUMMARY OF THE INVENTION

It is desirable that the problem described previously is solved.

One aspect of the invention provides an ultrasonic diagnostic apparatus for repeatedly performing a scan of transmitting ultrasonic beams to an image capture region in a subject and receiving an ultrasonic echo reflected from the image capture region, in a scan direction so as to correspond to the image capture region and, after that, on the basis of sound ray data obtained by performing the scans, generating an ultrasonic diagnosis image of the image capture region, including: an image correcting unit for performing a correcting process on the ultrasonic diagnosis image, wherein the image correcting unit executes an extracting process for extracting a sound ray vector image extending in a sound ray direction in which the ultrasonic beam is transmitted in the ultrasonic diagnosis image from the ultrasonic diagnosis image and, after that, performs the correcting process so as to eliminate the sound ray vector image extracted by the extracting process from the ultrasonic diagnosis image.

Another aspect of the invention provides an ultrasonic diagnostic image generating method for repeatedly performing a scan of transmitting ultrasonic beams to an image capture region in a subject and receiving an ultrasonic echo reflected from the image capture region, in a scan direction so as to correspond to the image capture region and, after that, on the basis of sound ray data obtained by performing the scans, generating an ultrasonic diagnosis image of the image capture region, including: an image correcting step of performing a correcting process on the ultrasonic diagnosis image, wherein in the image correcting step, an extracting process for extracting a sound ray vector image extending in a sound ray direction in which the ultrasonic beam is transmitted in the ultrasonic diagnosis image from the ultrasonic diagnosis image is executed and, after that, the correcting process is performed so as to eliminate the sound ray vector image extracted by the extracting process from the ultrasonic diagnosis image.

According to the invention, an ultrasonic diagnostic apparatus and an ultrasonic diagnostic image generating method realizing improvement in diagnostic efficiency by improving the quality of an ultrasonic diagnostic image can be provided.

Further objects and advantages of the present invention will be apparent from the following description of the preferred embodiments of the invention as illustrated in the accompanying drawings.

BRIEF DESCRIPTION OF THE DRAWINGS

FIG. 2 is a flowchart showing operations of the ultrasonic diagnostic apparatus 1 in the embodiment according to the invention.

DETAILED DESCRIPTION OF THE INVENTION

Apparatus

An ultrasonic diagnostic apparatus 1 of an embodiment according to the invention will be described.

Figure 1:
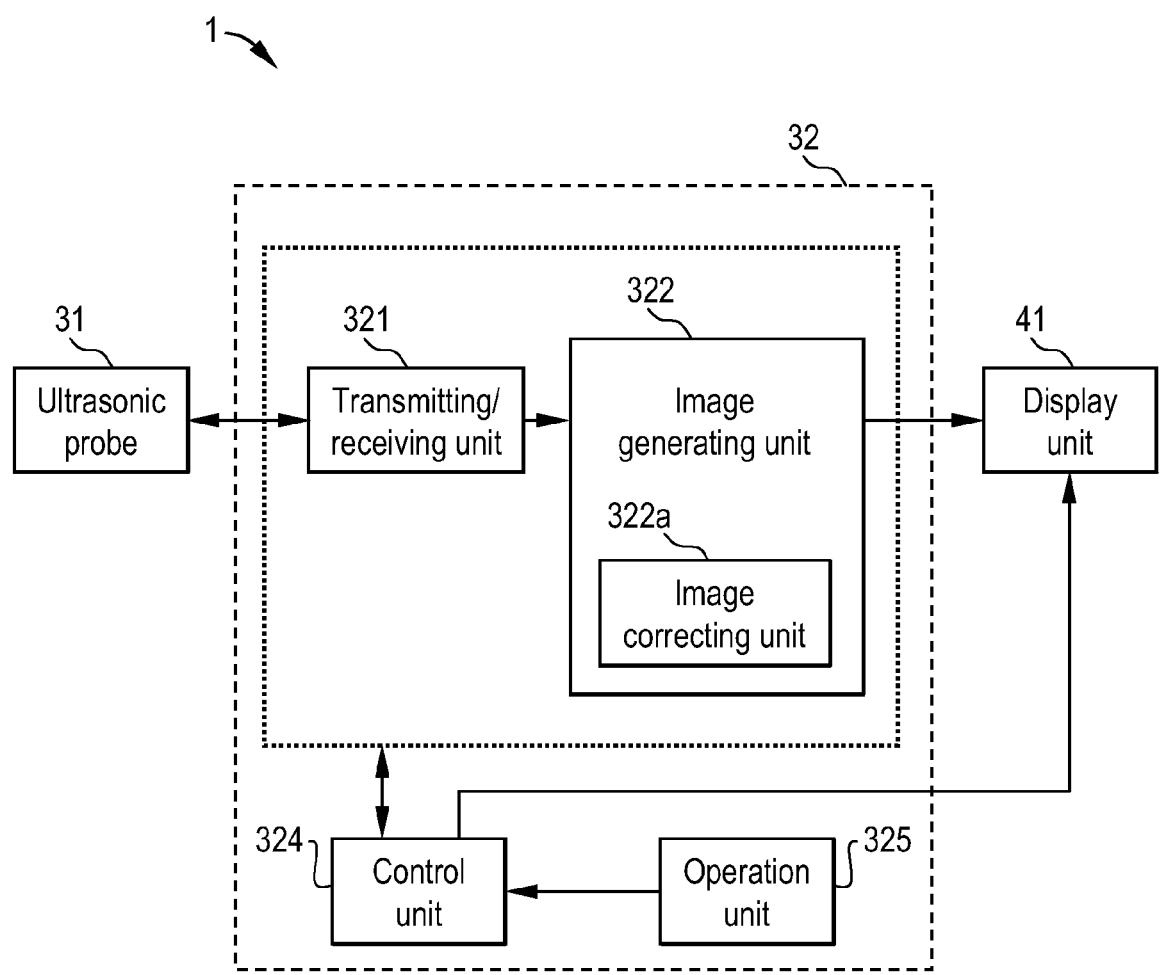
FIG. 1 is a block diagram showing the configuration of the ultrasonic diagnostic apparatus 1 in the embodiment according to the invention.

FIG. 1 is a block diagram showing the configuration of an ultrasonic diagnostic apparatus 1 in the embodiment of the invention.

As shown in FIG. 1, the ultrasonic diagnostic apparatus 1 of the embodiment has an ultrasonic probe 31, an operation console 32, and a display unit 41. The ultrasonic diagnostic apparatus 1 repeatedly scans an image capture region in a subject, by transmitting an ultrasonic beam to the image capture region and receiving an ultrasonic echo reflected from the image capture region in the scan direction and, after that, on the basis of sound ray data obtained by executing the scans, generates ultrasonic diagnosis images of the image capture region. The components will be described one by one.

The ultrasonic probe 31 is, for example, of a sector type and includes ultrasonic transducers (not shown). The ultrasonic transducers in the ultrasonic probe 31 are constructed so as to include, for example, a piezoelectric material such as lead zirconate titanate (PZT) ceramics. The ultrasonic transducers convert an electric signal to a sound wave, transmit the received sound wave, convert the received sound wave to an electric signal, and output the electric signal as an echo signal. The ultrasonic probe 31 is used in a state where the surface in which the ultrasonic transducers are formed is in contact with the surface of a subject. The ultrasonic probe 31 performs a scan by transmitting an ultrasonic beam into the subject in accordance with a drive signal from a transmitting/receiving unit 321 based on a control signal output from a control unit 324 in the operation console 32 and receiving an ultrasonic echo reflected from the subject to which the ultrasonic beam was transmitted, thereby obtaining an echo signal as raw data. The ultrasonic probe 31 outputs the echo signal to the transmitting/receiving unit 321.

The operation console 32 has, as shown in FIG. 1, the transmitting/receiving unit 321, an image generating unit 322, the control unit 324, and an operation unit 325. Each of the components of the operation console 32 includes a data processor, and the operation console 32 executes processes on various data.

The transmitting/receiving unit 321 includes a transmission/reception circuit for making the ultrasonic probe 31 transmit/receive an ultrasonic wave. On the basis of a control signal from the control unit 324, the transmitting/receiving unit 321 makes the ultrasonic probe 31 transmit an ultrasonic beam from the ultrasonic transducers to the subject, and makes the ultrasonic transducers receive an ultrasonic echo reflected from the subject, thereby generating an echo signal. For example, the transmitting/receiving unit 321 performs a scan on the subject by an electronic sector scan method and obtains an echo signal and outputs the obtained echo signal as sound ray data to the image generating unit 322. Concretely, the transmitting/receiving unit 321 obtains an echo signal by driving while switching the positions of the plurality of ultrasonic transducers in the ultrasonic probe 31 so as to scan the subject while moving an ultrasonic beam. The transmitting/receiving unit 321 performs processes such as amplification, delay, and addition on the echo signal, and outputs the resultant signal as sound ray data to the image generating unit 322.

The image generating unit 322 generates an ultrasonic diagnosis image of the image capture region in the subject on the basis of the sound ray data which is output from the transmitting/receiving unit 321. The image generating unit 322 is controlled by the control unit 324 in response to an instruction entered to the operation unit 325 and generates a B mode image, a CFM image, and the like as ultrasonic diagnosis images. The generated ultrasonic diagnosis images are temporarily stored in, for example, a cine memory (not shown) and, after that, are output and stored into an HDD (not shown).

In the embodiment, as shown in FIG. 1, the image generating unit 322 includes an image correcting unit 322a. The image correcting unit 322a executes a correcting process on the ultrasonic diagnosis image generated as described above. Concretely, after execution of an extracting process for extracting, from the ultrasonic diagnosis image, a sound ray vector image extending in the sound ray direction in which an ultrasonic beam is transmitted in the ultrasonic diagnosis image, the image correcting unit 322a performs the correcting process so as to eliminate the sound ray vector image extracted by the extracting process from the ultrasonic diagnosis image. For example, the correcting process is performed on the ultrasonic diagnosis image generated as a CFM image. As the details will be described later, first, at the time of performing the extracting process, a comparing process for comparing the pixel value of a first pixel arranged in the sound ray direction in the ultrasonic diagnosis image with the pixel value of a second pixel adjacent to the first pixel in the scan direction in the ultrasonic diagnosis image is sequentially executed on pixels arranged in the scan direction. After that, on the basis of the result of the comparing process, the first pixels are extracted as a sound ray vector image. At the time of performing the correcting process, the pixel values of the sound ray vector image extracted by the extracting process are corrected on the basis of sound ray data corresponding to the pixels adjacent to the sound ray vector image in the scan direction.

The control unit 324 includes, for example, a computer and a program for making the computer execute a predetermined data process and, on the basis of an operation signal from the operation unit 325, supplies control signals to the components to control the operations of the components.

The operation unit 325 includes, for example, a keyboard (not shown) and a track ball (not shown). Operation information is input by the operator to the operation unit 325. Based on the operation information, the operation unit 325 outputs an operation signal to the control unit 324. The operation unit 325 may be constructed by an input device such as a touch panel, a foot switch, or an audio input device.

The display unit 41 includes, for example, an LCD device (not shown) having a flat display screen and a DSC (Digital Scan Converter) (not shown), and displays an ultrasonic diagnosis image generated by the image generating unit 322. In the embodiment, a CFM image subjected to the correcting process of the image correcting unit 322a is displayed so as to be superposed on a B-mode image on the display screen.

Operations

Operations of the ultrasonic diagnostic apparatus 1 of the embodiment according to the invention will be described below.

FIG. 2 is a flowchart showing operations of the ultrasonic diagnostic apparatus 1 in the embodiment according to the invention. FIGS. 3A to 3D are diagrams for explaining the operations of the ultrasonic diagnostic apparatus 1 in the embodiment according to the invention.

First, as shown in FIG. 2, a scan is performed (S11).

The operator makes the surface in which the ultrasonic transducers are provided in the ultrasonic probe 31 come into contact with an image capture region in the subject. By performing a scan of transmitting an ultrasonic beam from the ultrasonic probe 31 into the subject and receiving an ultrasonic echo reflected from the subject to which the ultrasonic beam was sent by the ultrasonic probe 31, an echo signal is obtained as raw data. The echo signal is output to the transmitting/receiving unit 321. The transmitting/receiving unit 321 processes the echo signal as sound ray data and outputs the resultant.

Figure 3A:
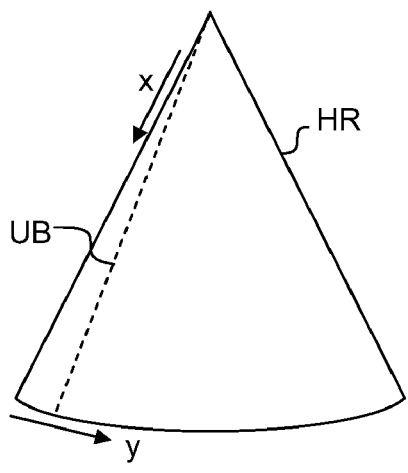
FIGS. 3(a), 3(b), 3(c), and 3(d) are diagrams for explaining the operations of the ultrasonic diagnostic apparatus 1 in the embodiment according to the invention.

FIG. 3A is a diagram showing a state where the scan is performed in the embodiment according to the invention.

In the embodiment, as shown in FIG. 3A, a scan is performed in the sector scan method. In this case, a scan of transmitting an ultrasonic beam UB to an image capture region HR in the subject along the sound ray direction "x" and receiving an ultrasonic echo reflected from the image capture region HR is repeatedly performed in the scan direction "y" so as to correspond to the image capture region. In other words, the ultrasonic beam UB is transmitted while being sequentially moved in a sector form in the scan direction "y" so as to be along the sound ray direction "x" corresponding to the depth direction of the subject in a position where the ultrasonic probe 31 is in contact with the image capture region HR in the subject. By receiving the ultrasonic echo reflected from the image capture region to which the ultrasonic beam UB was transmitted in predetermined time intervals, echo signals are sampled. The echo signal is processed as sound ray data by the transmitting/receiving unit 321 and the sound ray data is output to the image generating unit 322.

Next, as shown in FIG. 2, an ultrasonic diagnosis image is generated (S21).

In the embodiment, the image generating unit 322 generates an ultrasonic diagnosis image of the image capture region in the subject on the basis of the sound ray data which is output from the transmitting/receiving unit 321. For example, a B-mode image and a CFM image are generated as ultrasonic diagnosis images.

Next, as shown in FIG. 2, the process for correcting the ultrasonic diagnosis image is performed (S31).

The image correcting unit 322*a* corrects the ultrasonic diagnosis image generated as described above. Concretely, the extracting process for extracting a sound ray vector image extending in the sound ray direction in which the ultrasonic beam is transmitted in the ultrasonic diagnosis image from the ultrasonic diagnosis image is executed. After that, the correcting process is performed so as to eliminate the sound ray vector image extracted by the extracting process from the ultrasonic diagnosis image. In the embodiment, the correcting process is performed on an ultrasonic diagnosis image generated as a CFM image by performing a vector interpolation process.

Figure 3B:
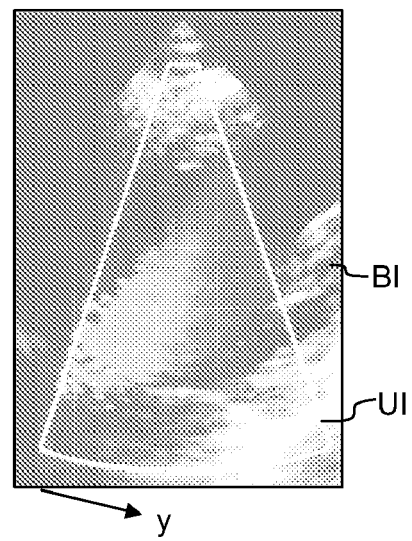

FIG. 3B is a diagram showing an ultrasonic diagnosis image obtained by superposing a CFM image on a B-mode image generated in the embodiment according to the invention. In the image, a sound ray vector image included in the CFM image is emphasized.

Since there is a case that ultrasonic beams neighboring in the scan direction "y" interfere each other on execution of the scan in an ultrasonic diagnosis image UI, as shown in FIG. 3B, a sound ray vector image BI may be generated as artifact extending in the sound ray direction "x" in which the ultrasonic beam is transmitted.

Consequently, first, an extracting process for extracting the sound ray vector image from the ultrasonic diagnosis image is performed.

In the embodiment, a comparing process for comparing the pixel value of a first pixel arranged in the sound ray direction in the ultrasonic diagnosis image and the pixel value of a second pixel adjacent to the first pixel in the scan direction in the ultrasonic diagnosis image is performed sequentially on pixels arranged in the scan direction. After that, on the basis of the result of the comparing process, the first pixels are extracted as a sound ray vector image.

Figure 3C:
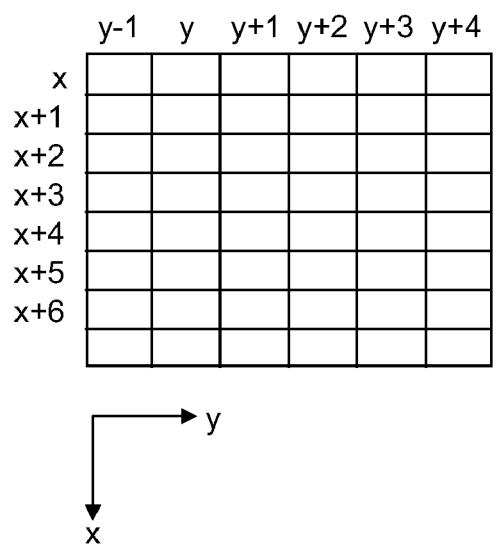

FIG. 3C is a diagram for explaining a state in which the sound ray vector image is extracted in the embodiment according to the invention.

In the embodiment, as shown in FIG. 3C, each of pixels arranged in the sound ray direction "x" and in the scan direction "y" in the ultrasonic diagnosis image is defined as ov[x][y]. A pixel position is specified in which the pixel value ov[x][y] of each of the first pixels in the ultrasonic diagnosis image satisfies the following mathematic expressions (1) and (2) in relation with the pixel values ov[x][y−1] and ov[x][y+1] of the second pixels adjacent to the first pixel. When the ov[x][y] is a positive value and mathematical expressions (3), (4), and (5) are satisfied, or when the ov[x][y] is a negative value and mathematical expressions (6), (7), and (8) are satisfied, the pixel position corresponding to the pixel value ov[x][y] is regarded as a start position for extracting a sound ray vector image.

In each of the mathematical expressions, q denotes a preset threshold, and abs( ) expresses a function for obtaining an absolute value. "i" is determined by an interference fringe pattern. The pattern varies depending on the apparatus, the presence or absence of simultaneous sound ray reception, the number of simultaneous reception times of sound rays, and the like. For example, when neighboring sound ray vectors cause an interference fringe in the sound ray direction due to acoustic interference, the brightness value is set according to a pattern such as a pattern (pattern A) in which brightness changes like 10, 5, 10, 5, . . . or a pattern (pattern B) in which brightness changes like 10, 8, 5, 8, 10, 8, 5, 8, 10, . . . ).

$$abs(ov[x][y]) > abs(ov[x][y-1]) \quad (1)$$

$$abs(ov[x][y]) > abs(ov[x][y+1]) \quad (2)$$

(in the case where ov[x][y] is a positive value)

$$ov[x][y] \geq q \quad (3)$$

$$ov[x][y+2i] \geq q \quad (4)$$

$$abs(ov[x][y+i]) < abs(ov[x][y]+ov[x][y+2i])*0.5 \quad (5)$$

(in the case where ov[x][y] is a negative value)

$$ov[x][y] \leq -q \quad (6)$$

$$ov[x][y+2i] \leq -q \quad (7)$$

$$abs(ov[x][y+i]) < abs(ov[x][y]+ov[x][y+2i])*0.5 \quad (8)$$

After that, the number of pixels included from the start position of extraction of the sound ray vector image specified as described above to the end of the sound ray vector image is counted. The counting is continued to the pixel having the pixel value satisfying the mathematical expressions (3), (4), (5), (6), (7), and (8), and a pixel group specified by the process is specified as a sound ray vector image. For example, as shown in FIG. 3C, in the case where the pixel of ov[x][y] is in the start position, the process is executed on pixels arranged in the sound ray direction "x" from the pixel in the start position, and a sound ray vector image is extracted from the ultrasonic diagnosis image.

Next, the correcting process is executed so as to eliminate the sound ray vector image extracted by the extracting process from the ultrasonic diagnosis image.

The pixel values of the sound ray vector image extracted by the extracting process are corrected on the basis of sound ray data corresponding to pixels adjacent to the sound ray vector image in the scan direction. For example, the correcting process is executed by a weighted average process.

In the embodiment, in the case where the number of pixels counted by the sound ray vector image extracted by the extracting process exceeds a predetermined threshold, the correcting process is performed. For example, in the case where the corrected pixel is defined as nv[x][y], with respect to an integer value "j" which is less than i and equal to or larger than 1, the correcting process is performed so as to satisfy the following mathematical expression (9). Xj and Xj′ denote weighting functions proportional to distances from ov[x][y+j] to ov[x][y]ov[x][y+2i] to be corrected. For example, as described above, in the case where the brightness value sequentially changes like 10, 5, 10, 5, . . . (pattern A) when an interference fringe occurs in the neighboring sound ray vectors in the sound ray direction due to the acoustic interference, each of xj and xj' is set to 0.5 (xj=0.5 and xj'=0.5). On the other hand, in the case where the brightness value sequentially changes like 10, 8, 5, 8, 10, 8, 5, 8, 10, . . . (pattern B) when an interference fringe occurs in neighboring sound ray vectors in the sound ray direction by the acoustic interference, the correcting process is executed so as to satisfy the following mathematical expressions (10), (11), and (12). That is, by varying the weighting functions for the pixel values of pixels neighboring the sound ray vector image in the scan direction in accordance with the distances from the sound ray vector image, the correcting process is performed.

$$nv[x][y+j]=ov[x][y]*Xj+ov[x][y+2i]*Xj' \quad (9)$$

$$nv[x][y+1]=ov[x][y]*0.75+ov[x][y+2i]*0.25 \quad (10)$$

$$nv[x][y+2]=ov[x][y]*0.5+ov[x][y+2i]*0.5 \quad (11)$$

$$nv[x][y+3]=ov[x][y]*0.25+ov[x][y+2i]*0.75 \quad (12)$$

As shown in FIG. 2, an ultrasonic diagnosis image is displayed (S41).

In the embodiment, the corrected ultrasonic diagnosis image is displayed on the display unit 41.

Figure 3D:
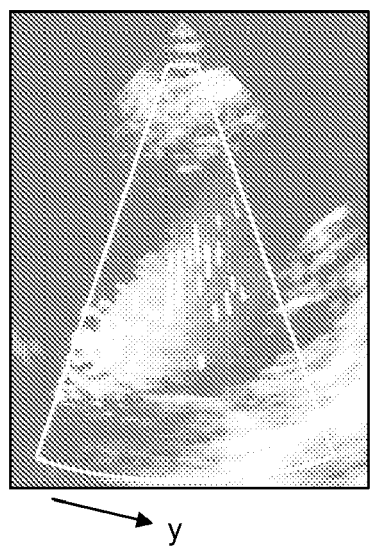

FIG. 3D is a diagram showing an ultrasonic diagnosis image displayed on the display unit 41 in the embodiment according to the invention.

In the embodiment, as shown in FIG. 3D, the CFM image corrected by the image correcting unit 322a is displayed so as to be superimpose on a B-mode image on the display screen.

As described above, in the embodiment, the extracting process is performed, for extracting a sound ray vector image extending in the sound ray direction "x" in which an ultrasonic beam is transmitted in the ultrasonic diagnosis image from the ultrasonic diagnosis image. After that, the correcting process is performed so as to eliminate the sound ray vector image extracted by the extracting process from the ultrasonic diagnosis image. Consequently, in the embodiment, the picture quality can be improved, so that the diagnosis efficiency at the time of performing an image diagnosis can be improved. It is particularly effective in the case where the ultrasonic diagnosis image is a color image such as a CFM image.

The invention is not limited to the foregoing embodiment but various modifications can be employed.

For example, although the case of correcting a CFM image as an ultrasonic diagnosis image has been described in the foregoing embodiment, the invention is not limited to the case. The invention can be also excellently applied to, for example, a B-mode image.

Many widely different embodiments of the invention may be configured without departing from the spirit and the scope of the present invention. It should be understood that the present invention is not limited to the specific embodiments described in the specification, except as defined in the appended claims.

The invention claimed is:

1. An ultrasonic diagnostic apparatus for repeatedly performing scans of, said ultrasonic diagnostic apparatus comprising:
an ultrasonic probe configured to transmit ultrasonic beams to an image capture region in the subject and receive an ultrasonic echo reflected from the image capture region, each scan performed in a scan direction corresponding to the image capture region;
an image generating unit configured to generate an ultrasonic diagnosis image of the image capture region based on sound ray data obtained by performing the scans; and
an image correcting unit configured to perform a correcting process on the ultrasonic diagnosis image, the correcting process including:
sequentially comparing a pixel value of a first pixel in a sound ray direction and pixel values of second pixels adjacent to the first pixel in the scan direction, the sound ray direction being a direction in which the ultrasonic beam is transmitted in the ultrasonic diagnosis image;
extracting the first pixels as a sound ray vector image based on a result of the sequence of comparisons by specifying a pixel position in which a pixel value ov[x][y] of the first pixel in the scan direction satisfies conditions:

$$abs(ov[x][y])>abs(ov[x][y-1]) \text{ and}$$

$$abs(ov[x][y])>abs(ov[x][y+1])$$

where abs( )expresses a function for obtaining an absolute value, x is the sound ray direction, y is the scan direction, ov[x][y] is the pixel value, and ov[x][y−1] and ov[x][y+1] are pixel values adjacent the pixel valve ov[x][y] in the scan direction;
correcting extracted pixel values of the sound ray vector image based on sound ray data corresponding to pixels adjacent to the sound ray vector image in the scan direction; and
eliminating the sound ray vector image extracted from the ultrasonic diagnosis image.

2. The ultrasonic diagnostic apparatus according to claim 1, wherein the image correcting unit is configured to set the pixel position corresponding to the pixel value ov[x][y] as a start position for extracting the sound ray vector image when the pixel value ov[x][y] is a positive value and $$ov[x][y] \geq q$$

$$ov[x][y+2i] \geq q \text{ and}$$

$$abs(ov[x][y+i])<abs(ov[x][y]+ov[x][y+2i])*0.5$$

where q is a preset threshold and i is a variable based on an interference fringe pattern of at least the ultrasonic diagnostic apparatus.

3. The ultrasonic diagnostic apparatus according to claim 1, wherein the image correcting unit is configured to set the pixel position corresponding to the pixel value ov[x][y] as a start position for extracting the sound ray vector image when the pixel value ov[x][y] is a negative value and $$ov[x][y] \leq -q$$

$$ov[x][y+2i] \leq -q \text{ and}$$

$$abs(ov[x][y+i])<abs(ov[x][y]+ov[x][y+2i])*0.5$$

where q is a preset threshold and i is a variable based on an interference fringe pattern of at least the ultrasonic diagnostic apparatus.

4. The ultrasonic diagnostic apparatus according to claim 2, wherein the image correcting unit is configured to extract a sound ray vector image from the ultrasonic diagnostic image starting at the pixel in the start position and proceeding to pixels arranged along a sound ray vector.

5. The ultrasonic diagnostic apparatus according to claim 3, wherein the image correcting unit is configured to extract a sound ray vector image from the ultrasonic diagnostic image starting at the pixel in the start position and proceeding to pixels arranged along a sound ray vector.

6. The ultrasonic diagnostic apparatus according to claim 1, wherein the ultrasonic diagnosis image comprises a color flow mapping image.

7. An ultrasonic diagnostic image generating method for repeatedly performing scans of a subject using an ultrasonic diagnostic apparatus, said method comprising:
    obtaining sound ray data by transmitting ultrasonic beams to an image capture region in the subject and receiving an ultrasonic echo reflected from the image capture region using an ultrasonic probe, the scans performed in a scan direction to correspond to the image capture region;
    generating an ultrasonic diagnosis image of the image capture region based on the sound ray data using an image generating unit; and
    correcting the ultrasonic diagnosis image using an image correcting unit by:
        repeatedly comparing a pixel value of a first pixel in a sound ray direction with pixel values of second pixels adjacent to the first pixel in the scan direction, the sound ray direction being a direction in which the ultrasonic beam is transmitted;
        extracting the first pixel as a sound ray vector image by specifying a pixel position in which a pixel value $ov[x][y]$ of the first pixel in the scan direction satisfies conditions:

$abs(ov[x][y]) > abs(ov[x][y-1])$ and $abs(ov[x][y]) > abs(ov[x][y+1])$ where abs( ) expresses a function for obtaining an absolute value, x is the sound ray direction, y is the scan direction, $ov[x][y]$ is the pixel value, and $ov[x][y-1]$ and $ov[x][y+1]$ are pixel values adjacent the pixel valve $ov[x][y]$ in the scan direction;
        correcting pixel values of the extracted sound ray vector image based on sound ray data corresponding to pixels adjacent to the sound ray vector image in the scan direction; and
        eliminating the extracted sound ray vector image from the ultrasonic diagnosis image.

8. The ultrasonic diagnostic image generating method according to claim 7, wherein correcting the ultrasonic diagnosis image further comprises setting the pixel position corresponding to the pixel value $ov[x][y]$ as a start position for extracting the sound ray vector image when the pixel value $ov[x][y]$ is a positive value and $ov[x][y] \geq q$ $ov[x][y+2i] \geq q$ and $abs(ov[x][y+i]) < abs(ov[x][y]+ov[x][y+2i])*0.5$ where q is a preset threshold and i is a variable based on an interference fringe pattern of at least the ultrasonic diagnostic apparatus.

9. The ultrasonic diagnostic image generating method according to claim 7, wherein correcting the ultrasonic diagnosis image further comprises setting the pixel position corresponding to the pixel value $ov[x][y]$ as a start position for extracting the sound ray vector image when the pixel value $ov[x][y]$ is a negative value and $ov[x][y] \leq -q$ $ov[x][y+2i] \leq -q$ and $abs(ov[x][y+i]) < abs(ov[x][y]+ov[x][y+2i])*0.5$ where q is a preset threshold and i is a variable based on an interference fringe pattern of at least the ultrasonic diagnostic apparatus.

10. The ultrasonic diagnostic image generating method according to claim 8, wherein extracting a sound ray vector image comprises extracting pixels arranged along a sound ray vector starting at a pixel in the start position as the sound ray vector image.

11. The ultrasonic diagnostic image generating method according to claim 9, wherein extracting a sound ray vector image comprises extracting pixels arranged along a sound ray vector starting at a pixel in the start position as the sound ray vector image.

12. The ultrasonic diagnosis image generating method according to claim 7, wherein generating an ultrasonic diagnosis image comprises generating a color flow mapping image.

* * * * *